United States Patent [19]

Takao et al.

[11] 4,155,828

[45] May 22, 1979

[54] OXYGEN SENSOR WITH A SINTERED REFERENCE SOURCE OF OXYGEN

[75] Inventors: Hiroshi Takao, Kamakura; Kazuo Matoba; Masaharu Ohshima, both of Yokohama, all of Japan

[73] Assignee: Nissan Motor Company, Limited, Yokohama, Japan

[21] Appl. No.: 827,734

[22] Filed: Aug. 25, 1977

[30] Foreign Application Priority Data

Sep. 22, 1976 [JP] Japan .................................. 51-114303

[51] Int. Cl.$^2$ ............................................. G01N 27/46
[52] U.S. Cl. ................................................. 204/195 S
[58] Field of Search ............................. 204/15, 195 S

[56] References Cited

U.S. PATENT DOCUMENTS

| | | | |
|---|---|---|---|
| 3,481,855 | 12/1969 | Kolodney et al. | 204/195 S |
| 3,768,259 | 10/1973 | Carnahan et al. | 204/195 S |
| 3,772,177 | 11/1973 | Rittiger et al. | 204/195 S |
| 3,819,500 | 6/1974 | Van Esdonk et al. | 204/195 S |
| 3,844,920 | 10/1974 | Burgett et al. | 204/195 S |
| 3,883,408 | 5/1975 | Kim et al. | 204/195 S |
| 3,915,830 | 10/1975 | Isenberg | 204/195 S |
| 3,940,327 | 2/1976 | Wagner et al. | 204/195 S |

OTHER PUBLICATIONS

Horsley, "Aere–R 3427," 1961, pp. 1–4 & FIG. 2.

*Primary Examiner*—T. Tung
*Attorney, Agent, or Firm*—Schwartz, Jeffery, Schwaab, Mack, Blumenthal & Koch

[57] ABSTRACT

An oxygen sensor comprises a solid electrolyte having one surface covered with a porous metallic film and the other surface on which a sinter of a metal and an oxide of the metal is disposed. Electromotive force (EMF) is developed between the film and the sinter during its use.

4 Claims, 3 Drawing Figures

OXYGEN SENSOR WITH A SINTERED REFERENCE SOURCE OF OXYGEN

FIELD OF THE INVENTION

The present invention relates in general to an electrochemical sensing device to determine oxygen content in a gas or a liquid by utilizing an ion conductive solid electrolyte as an oxygen concentration cell, and more particularly to an oxygen sensor particularly used for accommodation with a closed loop air-fuel mixture supply control system of an automotive internal combustion engine.

BACKGROUND OF THE INVENTION

It is known to use a mixture of oxygen-containing material, such as Ni-NiO mixture, Cd-CdO mixture or Zn-ZnO mixture, as an oxygen ion reference source of the oxygen sensor. Usually, the mixture is placed in a cavity formed in the electrolyte so as to electrically connect one surface defining the cavity to an electrode member immersed in the mixture, so that an electromotive force (EMF) is developed between the other surface of the electrolyte and the electrode member with a minimum electrical resistance. In such a conventional oxygen sensor, however, the oxygen-containing mixture is powdery (or sometimes a paste), so that a tight setting of the mass of the mixture in the cavity of the electrolyte is not expected because of its fluidity. Usually, some biasing means pressing the mass on the surface defining the cavity is employed for allowing the mass to maintain its original form inducing the assured electrical connection between the surface and the electrode member. However, since there is a limitation in ability to compress the powdery mixture of the oxygen-containing material, it sometimes happens that the mixture initially fixed becomes loose due to vibrations and heat hysteresis applied thereto during its use with a result that the electrical connection prepared by it becomes worse with increased electrical resistance. In addition to this, in the prior art oxygen sensor mentioned above, some sealing means is required to prevent the powdery mixture of the oxygen-containing material from being lost through any slit formed in the sensor. This induces increased production costs of the sensor. Consequently, the prior art oxygen sensor mentioned above is somewhat impractical due to the drawbacks.

SUMMARY OF THE INVENTION

Therefore, the present invention contemplates to eliminate the above-described several drawbacks of the prior art oxygen sensor.

It is an object of the present invention to provide a new and improved oxygen sensor which has therein a solid mass of oxygen-containing material acting as an electrode, the solid mass being a sinter of a metal and an oxide of the metal.

According to the present invention, there is provided an oxygen sensor for determining the oxygen content in a fluid, comprising a casing, a solid electrolyte disposed in the casing and having first and second surfaces which are exposed to the fluid and to a reference source of oxygen, respectively, a porous metallic electrode covering the first surface of the electrolyte, and a sinter of a metal and an oxide of the metal which sinter is disposed on the second surface of the electrolyte to function as the reference source of oxygen.

BRIEF DESCRIPTION OF THE DRAWINGS

Other objects and advantages of the present invention will become apparent from the following description when taken in conjunction with the accompanying drawings, in which.

DESCRIPTION OF THE PREFERRED EMBODIMENTS

Figure 1:
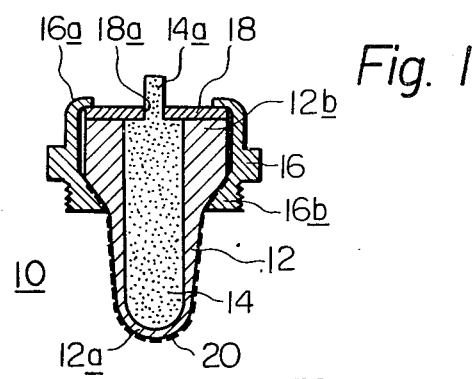
FIG. 1 is a sectional view of a first preferred embodiment according to the present invention.

Referring to FIG. 1 of the drawings, there is shown an oxygen sensor of the invention, as generally designated by numeral 10. The sensor 10 comprises a tubular solid electrolyte 12 having one end 12a closed and the other end 12b open, the thickness of the closed end 12a being about 0.5 mm. The solid electrolyte 12 thus far provided may consist of $ZrO_2$ stabilized by CaO, $Y_2O_3$, SrO, MgO or $ThO_2$, or $Bi_2O_3$ stabilized by $Nb_2O_5$, SrO, $WO_3$, $Ta_2O_5$ or $Y_2O_3$. In addition, the electrolyte may be constructed of a mixture of $ThO_2$ and $Y_2O_3$, or a mixture of CaO and $Y_2O_3$. Snugly disposed in the interior of the electrolyte 12 is a cylindrical block having a diameter of about 8 mm which is a sintered oxygen-containing mass 14 prevailing in the invention. The mass 14 may consist of a mixture of Ni-NiO, Cd-CdO, Zn-ZnO, Cu-$Cu_2O$, Co-CoO or Cr-$Cr_2O_3$. Each of the mixtures may be made of 1 to 99% metal composition and 99 to 1% metal oxide composition. Experiments have revealed that the mixture of Ni-NiO is best in this invention. Indicated by numeral 16 is a metallic casing which holds therein the electrolyte 12 and fixes the same thereto by inwardly bending an upper end 16a thereof to urge the electrolyte 12 downwardly with respect to a lower end 16b thereof via an insulating plate 18. The metallic casing 16 may be constructed of a stainless steel such as AISI 304 or AISI 430. The insulating plate 18 may be made of alumina, mullite, alumina-silicate, forsterite or spinel. The sintered oxygen-containing mass 14 is formed with a projection 14a extending outwardly and passing through an opening 18a formed in the insulating plate 18. If desired, the projection 14a may be replaced by a metallic terminal member immersed at its one end into the mass 14. The outer surface of the electrolyte 12 is covered with a suitable porous metallic electrode 20 which is, for example, a platinum film having a thickness of about 2 microns. Instead of the platinum film having catalytic oxidation promoting properties, other films devoid of catalytic oxidation promoting properties such as Ag, Au and SiC are usable. Furthermore, platinum group metals having catalytic oxidation promoting properties, such as Ru, Rh, Pd, Os and Ir, are also usable for the electrode 20, and alloys of platinum group metals and base metals are also employable as the electrode 20. The deposition of such electrode 20 on the surface of the electrolyte 12 is accomplished by several methods, such as a plasma-jet coating method, as will be described more fully hereinbelow.

With this construction of the oxygen sensor 10 equipped with the solid or sintered oxygen-containing mass 14 according to the invention, the following merits and advantages are given. First, the electrical connection of the inner surface of the electrolyte 12 and the mass 14 is reliably achieved only by pressing one portion of the mass 14 against the electrolyte 12. This electrical connection will be assuredly maintained even when subjected to severe vibrations. Second, the sealing means such as the one previously mentioned is unnecessary. Third, due to the solidity of the mass 14, the assembling process of the sensor 10 is remarkably facilitated.

Figure 2:
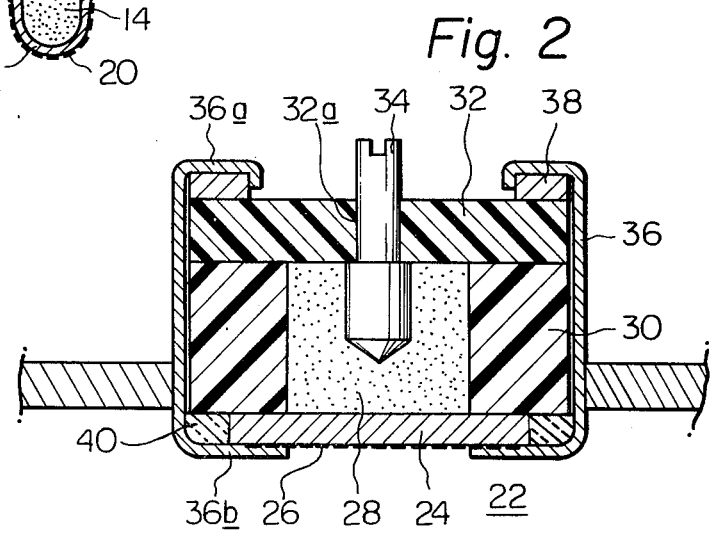
FIG. 2 is a sectional view of a second preferred embodiment of the invention.

Referring to FIG. 2, there is illustrated a second embodiment of the oxygen sensor according to the invention, the sensor being generally designated by numeral 22. The oxygen sensor 22 comprises a disc-shaped solid electrolyte 24 having a thickness of about 1 mm. An outside surface of the electrolyte 24 is coated with a porous metallic film 26 such as platinum film having a thickness of about 2 microns. Coaxially disposed on an inside or upper surface of the electrolyte 12 is a cylindrical oxygen-containing mass 28 which is sintered. The sintered mass 28 is formed to have an external diameter of about 8 mm and a height of about 8 mm. Concentrically disposed around the sintered mass 28 is an annular insulating member 30 which has a lower surface contacting the inside surface of the electrolyte 24 and an upper surface flush with an upper surface of the mass 28, as shown. A disc-shaped insulating plate 32 is coaxially disposed on the upper surfaces of the sintered mass 28 and the insulating member 30. A metallic terminal member 34 is immersed at its lower enlarged end portion into the sintered mass 28 and is projected outwardly at its upper end portion passing through an opening 32a formed in the insulating plate 32. The opening 32a is smaller in diameter than the enlarged end portion of the metallic terminal member 34. A cylindrical metallic casing 36 having inwardly bent upper end lower portions 36a and 36b holds therein a unit of the electrolyte 24, the sintered mass 28, the insulating member 30, the insulating plate 32 and the terminal member 34 and tightly fixes it thereto by using a ring 38 made of stainless steel. As shown, the inwardly bent lower portion 36b contacts the porous metallic film 26 on the electrolyte 24. A circular space (no numeral) defined around the disc-shaped electrolyte 24 in the casing 36 is filled with a glassy sealing material 40, such as a mixture of 70% PbO, $B_2O_3$ and $SiO_2$, to prevent a gas or a liquid contacting the metallic film 26 from penetrating into the sintered mass 28. With this construction, the electromotive force (EMF) is developed between the terminal member 34 and the casing 36 during the use of the sensor 22.

Figure 3:
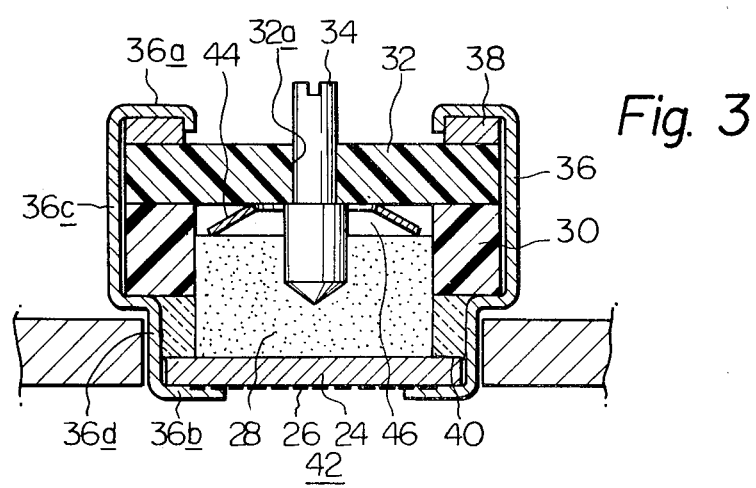
FIG. 3 is a sectional view of a third preferred embodiment of the invention.

Referring to FIG. 3, there is illustrated a third preferred embodiment of the present invention. For facilitation of description, the generally same parts are designated by the same numerals as in the case of the second preferred embodiment of FIG. 2. As will be apparent from the following description, the sensor 42 of this third embodiment is equipped with biasing means 44 used for forcedly pressing the sintered oxygen-containing mass 28 onto the inner surface of the electrolyte. The sensor 42 comprises a disc-shaped electrolyte 24 having a thickness of about 1 mm. An outer or lower surface of the electrolyte 24 is covered with a porous metallic film 26 of about 2 microns in thickness. Coaxially disposed on an inner or upper surface of the electrolyte 24 is a sintered oxygen-containing mass 28 which is cylindrical. The height of the mass 28 is about 6 mm and the outer diameter of it is about 8 mm. Concentrically disposed around the mass 28 is a ring-shaped insulating member 30. As shown, insulating member 30 is arranged to project upwardly at a certain distance from an upper surface of the sintered mass 28. A disc-shaped insulating plate 32 is coaxially disposed on an upper surface of the insulating member 30 to define a cylindrical space 46 between it and the upper surface of the sintered mass 28. A metallic terminal member 34 is immersed at its lower enlarged end portion into the sintered mass 28 and is projected outwardly at its upper end portion passing through an opening 32a formed in the insulating plate 32. A cylindrical metallic casing 36 having inwardly bent upper and lower portions 36a and 36b holds therein a unit of the electrolyte 24, the sintered mass 28, the insulating member 30 and the terminal member 34 and tightly fixes it thereto by disposing a stainless steel ring 38 between the insulating plate 32 and the inwardly bent upper end portion 36a of the casing 36. As shown, the casing 36 of this embodiment is formed to have a large diameter portion tightly receiving the insulating member 30, the insulating plate 32 and the ring 38, and a small diameter portion 36d snugly receiving the electrolyte 24. A circular space (no numeral) defined around the sintered mass 28 and between the electrolyte 24 and the insulating member 30 in the casing 36 is filled with a glassy sealing material 40. In addition to the above elements, the disc spring 44 is disposed in the cylindrical space 46 to press the sintered mass 28 to the inner surface of the electrolyte 24. If desired, a different spring (not shown) may be used in place of the disc spring 44. With this construction of the oxygen sensor 42 equipped with the spring 44, the following additional merits and advantages are achieved. First, the concentration of stress applied to the electrolyte 24 will be substantially eliminated, so that the electrolyte 24 is never broken during its use. Second, the thermal expansion of the sintered mass 28 is absorbed by the spring 44 so that breakage of the mass 28 does not occur.

In order to more clarify the invention, the following several Examples will be given.

EXAMPLE 1

To prepare an oxygen sensor such as one shown in FIG. 1, the following method was used. A solid solution of 85 mole % $ZrO_2$ and 15 mole % CaO was used for the formation of the tubular electrolyte 12 having one end closed. A mixture of 44 Wt. % Ni and 56 Wt. % NiO was compressed at about 5000 Kg/cm$^2$ at room temperature to provide a shaped body, and then the body was baked at about 1400° C. for about 1 hr in an atmosphere of nitrogen. With this, the density of the baked body was about 6.5 g/cm$^3$ (theoretical value is about 8.2 g/cm$^3$), and the bending resistance of it was about 800 kg/cm$^2$. The baked or sintered body was then shaped or cut into a form substantially the same as the inner cylindrical space of the electrolyte 12, and then the cylindrically shaped sintered body was thrust into the space. The insulating plate 18 was made of $Al_2O_3$ and the casing was of stainless steel (AISI 304). The electrode 20 was prepared by coating the outer surface of the electrolyte 12 with a paste containing platinum powder dispersed in an organic binder and then baking the coated electrolyte at about 1000° C. for about 1 hr. With this, excellent performance and durability were obtained in the sensor.

EXAMPLE 2

To prepare an oxygen sensor such as one shown in FIG. 2, the following procedure was used. The electrolyte 24 was made of a solid solution of 10 mole % Y$_2$O$_3$ and 90 mole % ZrO$_2$. The cylindrical sintered mass 28 was produced from a Ni-NiO mixture by using the beforementioned sintering technique with respect to Example 1. Al$_2$O$_3$ was used for the formation of the insulators 30 and 32, and a stainless steel (AISI 304) was used for the casing 36. The metallic film 26 and the metallic terminal member 34 were made of platinum and a stainless steel (AISI 430) respectively. Satisfactory performance and durability were obtained also in this sensor.

EXAMPLE 3

The same procedure was followed as in Example 2, but with an exception that the electrolyte 24 was made of a solid solution of 15 mole % Nb$_2$O$_5$ and 85 mole % Bi$_2$O$_3$. Substantially the same performance and durability were obtained as in Example 2.

EXAMPLE 4

To prepare an oxygen sensor such as one shown in FIG. 2, the following procedure was used. Substantially the same procedure was followed as in Example 2 except for the formation of the sintered oxygen-containing mass 28. In this Example, the sintered mass 28 was produced by using a "hot press method" in which a mixture of 44 Wt % Ni and 56 Wt % NiO is compressed under about 300 kg/cm$^2$ at 1200° C. for about 10 min. With this method, the density of the produced sintered mass was about 7.8 kg/cm$^3$ (theoretical value is about 8.2 g/cm$^3$), and the bending resistance of it was about 1300 kg/cm$^2$. The performance and durability of the sensor according to this Example were substantially the same as in Example 2.

EXAMPLE 5

To prepare an oxygen sensor such as one shown FIG. 3, the following procedure was used. The electrolyte 24 was made of a solid solution of 10 mole % Y$_2$O$_3$ and 90 mole % ZrO$_2$, and the cylindrical sintered mass 28 was produced from a mixture of 44 Wt % Ni and 56 Wt % NiO by using substantially the same forming technique as in Example 2. The insulators 30 and 32 were made of Al$_2$O$_3$, and the casing 36 was of stainless steel (AISI 430). Platinum was used for the formation of the film 26, and a stainless steel (AISI 430) was used for the terminal member 34. A disc spring disposed in the space 46 was made of stainless steel (AISI 304-CSP). Satisfactory performance and durability were obtained also in this sensor.

EXAMPLE 6

The same procedure was followed as in Example 5, but with the exception that the disc spring was replaced by a coil spring made of a stainless steel wire (AISI 631-WPC) having a diameter of 0.8 mm. Substantially the same performance and durability were obtained as in Example 5.

With the above-stated constructions of the oxygen sensor according to the present invention, the following characteristic effects are obtained:

(1) Since the oxygen-containing mass, such as a Ni-NiO mixture, is formed into a sinter having a high mechanical strength, the reliable electrical connection between the electrolyte and the solid mass is readily achieved by only pressing a portion of the solid mass onto the electrolyte.

(2) Since the sintered oxygen-containing mass has a higher electrical conductivity in comparison with the powdery mass, the sintered mass can be used as a so-called inner electrode which is usually a porous metallic film covering a surface of the electrolyte exposed to a reference gas. This means facilitation of the production process of the oxygen sensor and the simplification of the same inducing a low cost of manufacturing.

(3) The sintered oxygen containing mass has a greater amount of metal oxide or metal oxides per unit volume in comparison with the powdery mass. This means that the sintered mass has a relatively long life.

(4) In the sensor shown in FIG. 3 having the biasing means, the concentration of stress applied to the electrolyte is eliminated, so that the electrolyte is never broken during its use. The thermal expansion of the sintered mass caused, for example, by exposing it to a higher temperature fluid will be absorbed, so that the breakage of the mass is prevented.

What is claimed is:

1. An oxygen sensor for determining the oxygen content in a fluid, comprising:
   a cylindrical metallic casing having a first inwardly bent portion at one end thereof and a second inwardly bent portion at the other end thereof;
   a disc-shaped solid electrolyte coaxially disposed in said casing so that the outwardly facing flat surface thereof contacts with said first inwardly bent portion;
   a porous metallic film coated on said outwardly facing surface of said solid electrolyte disc;
   a cylindrical sinter mass of a metal and an oxide of the metal, said sinter mass functioning as a reference source of oxygen and being coaxially disposed on the inside facing flat surface of said solid electrolyte disc;
   an annular insulating member disposed in said casing in a manner coaxially surrounding said sinter mass;
   a disc-shaped insulating plate having an aperture therethrough disposed in said casing on the side of said sinter mass opposite said solid electrolyte disc in a manner to enclose said sinter mass with the aid of said annular insulating member and said electrolyte;
   a ring member arranged between said second inwardly bent portion of said casing and the outside surface of said insulating plate, for achieving tight assemblage of the parts in the casing; and
   a metallic terminal member including an enlarged section immersed in said sinter mass and an elongated section passing through the aperture in said insulating plate, the cross sectional area of said enlarged section of said metallic terminal member being larger than that of the aperture.

2. An oxygen sensor as claimed in claim 1, wherein said first inwardly bent portion of said casing is in contact with said porous metallic film.

3. An oxygen sensor as claimed in claim 1, further comprising biasing means operatively disposed in a clearance defined between said disc-shaped insulating plate and said cylindrical sinter mass for biasing said sinter mass against said electrolyte.

4. An oxygen sensor as claimed in claim 3, wherein said biasing means comprises a disc spring.

* * * * *